United States Patent [19]
Gelfand et al.

[11] Patent Number: 5,270,052
[45] Date of Patent: Dec. 14, 1993

[54] METHODS AND COMPOSITIONS FOR TREATMENT OF INFECTION BY INTRACELLULAR PARASITES

[75] Inventors: Jeffrey A. Gelfand; Michael V. Callahan, both of Cambridge, Mass.; Yoshinori Yamada, Tokyo, Japan

[73] Assignee: New England Medical Center Hospitals, Inc., Boston, Mass.

[21] Appl. No.: 689,709

[22] Filed: Apr. 19, 1991

[51] Int. Cl.$^5$ .............................. A61K 9/127
[52] U.S. Cl. .................... 424/450; 436/829; 514/21
[58] Field of Search ............... 424/85.1, 450; 436/829; 514/21; 428/402.2

[56] References Cited

U.S. PATENT DOCUMENTS

| | | | |
|---|---|---|---|
| 4,812,312 | 3/1989 | Lopez-Berestein et al. | 424/450 X |
| 4,857,314 | 8/1989 | O'Connor et al. | 424/85.1 |
| 4,944,948 | 7/1990 | Uster et al. | 426/450 |

OTHER PUBLICATIONS

Deodhar et al., Cancer Res., 42, 5084–5088 (1982).
Mold et al., J. Exp. Med., 154, 1703–1708 (1981).
Kirsh et al. Annals of NY Academy of Science 507, p. 141, 1987.
Deodhar Cancer Res. (1), 5084 (1982).
Mold J. Exp. Med. 154, 1703 (1981).
Ryman, Clinical Pharmacology, 5:91, 1975.
Davis et al. Biological Approaches to the Controlled Delivery of Drugs, Juliano (Ed.) New York Academy of Sciences, New York, 1987.
Kirsch et al., Biological Approaches to the Controlled Delivery of Drugs, Juliano (Ed.) New York Academy of Sciences, New York, 1987.
International Search Report dated Jul. 21, 1992 for PCT/US92/03166.

*Primary Examiner*—Thurman K. Page
*Assistant Examiner*—G. S. Kishore
*Attorney, Agent, or Firm*—Fish & Richardson

[57] ABSTRACT

A method for treating an infection caused by an intracellular parasite in a patient. The method includes administering to the patient liposomes coated with C-reactive protein, wherein the liposomes include phosphatidylcholine or phosphorylcholine.

4 Claims, 1 Drawing Sheet

METHODS AND COMPOSITIONS FOR TREATMENT OF INFECTION BY INTRACELLULAR PARASITES

The Government has rights in this invention pursuant to grant No. R01HD19675 awarded by the National Institutes of Health.

BACKGROUND OF THE INVENTION

This invention relates to the treatment of infection caused by parasites which infect monocytes/macrophages or neutrophils.

Liposomes are small fluid-filled lipid spheres composed of a bilayer of amphipathic lipids (e.g., phospholipids). Liposomes can be filled with a variety of molecules and because they are only partially permeable, they have been proposed as a means for targeting drugs directly to cells and thus avoid dilution or degradation of the drug in body fluids (See Ryman, *Clinical Pharmacology* 5:91, 1975; Davis et al., in *Biological Approaches to the Controlled Delivery of Drugs,* Juliano (ed.) New York Academy of Sciences, N.Y., 1987). The fact that for most part liposomes are unable to leave the general circulation has limited their application as a drug delivery system. Liposomes are generally removed from the circulation by cells of the reticuloendothelial system. This circulatory system is composed of monocytes/macrophages and other phagocytic cells which take up liposomes. This "passive" targeting of liposomes to mononuclear phagocytes has led to the suggestion that liposomes might be well suited to delivery of drugs to these cells (Kirsh et al., in *Biological Approaches to the controlled Delivery of Drugs,* Juliano (ed.) New York Academy of Sciences, N.Y., 1987).

C-reactive protein (CRP) is protein released by the liver in response to tissue damage.

SUMMARY OF THE INVENTION

In general, the invention features a method for treating an infection caused by an intracellular parasite in a patient the method includes administering to the patient liposomes coated with C-reactive protein, wherein the liposomes include phosphatidylcholine or phosphorylcholine. By "parasite" is meant any microorganism which infects cells. The term includes, but is not limited to, mycobacteria, and viruses. The term "liposome" is meant to include uni- and multi-lamellar vesicles and lipid emulsions.

In preferred embodiments, the liposomes contain a drug directed against said parasite; the parasite is a bacteria; the parasite is a fungi; the parasite is a 5 mycobacteria; the parasite is a virus; the parasite is mycobacterium avium intracellulare; the parasite is chlamydia; and the parasite is mycobacterium tuberculosis.

In a related aspect, the invention features a pharmacologically acceptable mixture comprising C-reactive protein and phosphatidylcholine or phosphorylcholine.

In another related aspect, the invention features a method for the treatment of a parasitic infection in a patient which is receiving nourishment enterally; the method includes administering a pharmacologically acceptable mixture comprising phosphatidylcholine or phosphorylcholine to the patient.

In yet another related aspect, the invention features a method for the treatment of a parasitic infection in a patient; the method includes measuring the endogenous level of C-reactive protein in the serum of the patient and, if the level C-reactive protein is at or above 500 µg/ml, administering a pharmacologically acceptable mixture comprising phosphatidylcholine or phosphoserine to the patient, or, if the level of C-reactive protein is below 500 µg/ml, administering a pharmacologically acceptable mixture which includes C-reactive protein and phosphatidylcholine or phosphorylcholine to the patient.

Other features and advantages of the invention will be apparent from the following description of the preferred embodiments thereof, and from the claims.

DETAILED DESCRIPTION OF THE DRAWINGS

The drawings are first briefly described.

Figure 1:
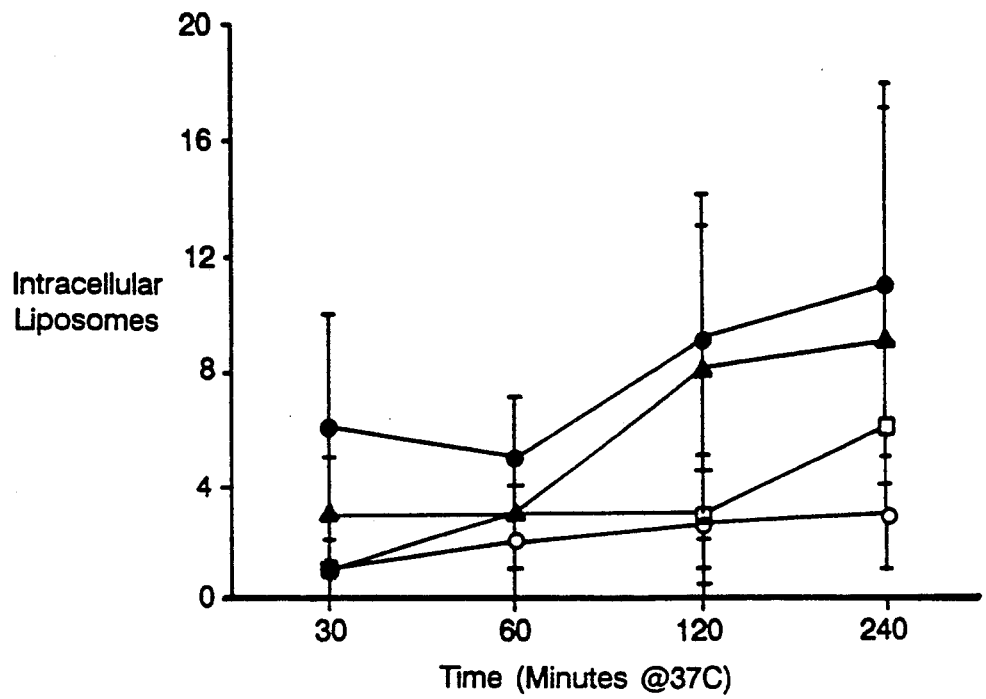
FIG. 1 depicts a graph which illustrates the time dependent phagocytosis of liposomes by macrophages. Lipisin II was prepared with no C-reactive protein (open circles), with 125µg/ml C-reactive protein (open squares), with 500µg/ml C-reactive protein (filled triangles), or with 800 µg/ml C-reactive protein (filled circles).

Drug Delivery Using C-Reactive Protein Coated Liposomes

The experiments described below demonstrate that C-reactive protein can be used to efficiently target liposomes to monocytes/macrophages and that these CRP coated liposomes can be used to effectively target a drug to monocyte/macrophages infected with an intracellular parasite.

C-reactive protein-coated liposomes can be used to deliver drugs to monocytes/macrophages and neutrophils. Accordingly, such liposomes can be used as therapy for any pathogen that infects these cells including mycobacterium avium intracellular, leishmania and Human Immunodeficiency Virus. Some of the pathogens which infect monocytes/macrophages are listed in Table 1 along with some of the drugs used for treatment of these infections. This listing is not meant to limit the invention. Because C-reactive protein sharply increases the targeting of liposomes to monocytes/macrophages and neutrophils, in many cases it will be possible to use drug dosages that are substantially lower than those used in conventional therapy. Preferred drugs are those drugs which are directed to the parasite as opposed to drugs which are primarily cytotoxins.

| Pathogen | Drug |
| --- | --- |
| Mycobacterium tuberculosis | pyrazinamide, streptomycin, cycloserine |
| Mycobacterium avium Intracellulare | clofazimine, cycloserine, amikacin, rifabutin |
| Mycobacterium leprae | dapsone, clofazimine, thalidomide |
| Brucella abortus | doxycycline, gentamycine, trimethaprim sulfamethoxazol |
| Yersinia | streptomycin, tetracycline, chloramphenicol |
| Nocardia | minocycline, amikacin |

-continued

| Pathogen | Drug |
| --- | --- |
| Legionlla | erythromycin, Rifampin, tetracycline |
| Listeria | tetracycline, chloramphenicaol, trimethaprim sulfamethoxazole |
| Salmonella | chloramphenicol, trimethaprim sulfamethoxazole |
| Chlamydia | tetracycline, doxycycline, erythromycin |
| Rickettsia | chloramphenicol, tetracycline |
| Borrelia | erythromycin, tetracycline |
| Leishmania | stibogluconate, methylbenzonium, chloride |
| Toxoplasma | pyrimthamine, spiramycin, clindamycin |
| Trypanosoma | suramin, pentamidine |
| Histoplasma | amphotercin B |
| Cryptococcus | amphotercin B, fluconazol |
| Aspergillus | itraconazol, amphotercin B |
| Blastomycosis | ketaconazole, amphotercin B |
| Human Immunodeficiency Virus (HIV) | AZT, dDC, dDi |
| Influenza virus | rimantidien |

Many methods for preparing liposomes are known to those skilled in the art (U.S. Pat. Nos. 4,229,360, 4,247,411, 4,311,712 and 4,830,858). Useful liposomes may be prepared by any convenient method. In addition, lipid emulsions of the oil-in-water type, water-in-oil type or water-in-oil-in-water type may also be used (Davis et al., supra). It is important that phosphorylcholine or, preferably, phosphatidylcholine be present as part of the liposome or emulsion, since these molecules provide a binding site for C-reactive protein. For liposomes and lipid emulsions containing phosphatidylcholine, it is preferred that they be at least 1.7% phosphatidylcholine. Generally, the higher the proportion phosphatidylcholine, the more CRP can be coated onto the surface. Useful liposomes may be multilamellar vesicles, small unilamellar vesicles or large unilamellar vesicles. Generally the drug will be introduced into the liposome in any standard manner (e.g., by sonication), and drug incorporation may occur subsequent to coating with CRP. Preferably liposomes are smaller than 400 nM in diameter; more preferably they are less than 200 nM in diameter. Liposomes are coated with CRP by incubation with CRP as described below. A solution of 800 μg/ml CRP is preferred for coating liposomes but lower concentrations may also be used.

Treatment of Parasitic Infections Using C-Reactive Protein Coated Liposomes

CRP coated liposomes or lipid emulsions bound with CRP can be used without drugs to stimulate monocytes/macrophages and neutrophils. Purified monocytes infected with Leishmania mexicana were found to be activated to kill intracellular amastigotes upon inculation with liposomes and CRP. Treatment with liposomes incubated with CRP at 500 μg/ml CRP (excess CRP was removed by washing) decreased infection by 53% compared to untreated control cells. When used alone, CRP or liposomes increased infection by up to 20% compared to control cells.

Because liposome-bound CRP is so immunostimulatory it may be used for treatment on intracellular parasitic infections without the addition of a conventional anti-parasite drug. Although many infected patients have elevated CRP levels, in most cases it will be necessary to treat the patient with a combination of liposome and CRP. For treatment with liposomes only it is preferred that the intracellular CRP level be at least 500 μg/ml. When the CRP level is lower it is preferred that liposomes be treated with CRP prior to administration.

Commercially available lipid or liposome preparations, e.g., Lipisin II (Abbott, Chicago, Ill.) may be used as long as they contain phosphorylcholine or, preferably, phosphatidylcholine. The liposomes are coated with CRP as described below. It is not required that the excess (i.e. unabsorbed) CRP be washed out of the liposome solution.

CRP coated liposomes was found to increase the tumoricidal activity of monocytes. Accordingly CRP coated liposomes can be used for treatment of cancer. They may also be used as described above to deliver chemotherapeutic agents.

Purification of phosphorylcholine

Chromatographically homogenous phosphatidylcholine (PC) was prepared from hen egg yolk. Egg yolk was separated from egg white and vigorously mixed with a 2 volumes of a 2:1 solution of chloroform-methanol for 1 hour at 4° C. followed by overnight lyophilization at room temperature. A partially purified PC fraction was produced by recrystallization in a 1:3 mixture of acetone-petroleum ether. Crude PC crystals were dissolved in 2 volumes of chloroform and loaded onto a 25×1.5 cm alumina column equilibrated in chloroform and stored at 4° C. Following loading, the column was washed extensively with 10 bed volumes of chloroform, and partially purified PC was eluted by an increasing linear gradient of methanol. Fractions rich in PC were identified by treatment with Dragendorff's reagent (Sigma Chemical Co., St. Louis, MO) and pooled. The PC-rich fraction was further purified by loading I ml volumes onto a 40×1.5 cm silicic acid column and washing with 2 bed volumes of chloroform at 4° C. Purified PC was eluted by increasing linear gradient of methanol. Purity of isolated PC fractions was determined by silica gel thin layer chromatography using a chloroform-methanol-acetic acid mixture (50:30:9) as solvent. PC-rich lipids were again visualized by spraying sample aliquots with Dragendorff's reagent, and by exposure to iodine vapors. Chromatographically-pure fractions were recrystalized from acetone and stored under nitrogen or argon-saturated acetone at −75° C.

Preparation of unilamellar PC-liposomes

Purified egg PC was warmed to room temperature and dissolved in 100 benzene and vigorously agitated for 30 minutes. Following agitation, the mixture was lyophilized for 8 h at room temperature. Lyophilized lipid was dissolved in 100 mM KCl, 10 mM Tris-HCl (pH 8) (Buffer A), and adjusted to a final concentration of 3%. The suspension was then sonicated for 60 minutes using a 20 kc Bronson sonicator under 100% argon at 4–6° C. Following sonication, sample aliquots are tested for complete conversion of large multilamellar vesicles to small unilammelar vesicles using a Beckman 16HV light spectrophotometer. Following complete conversion to unilamellar vesicles, unsonicated lipid, and titanium released from the sonicator tip, were removed by centrifugation at 100,000g (4° C.) for 120 minutes for each 10 mls of lipid mixture. The supernatant was concentrated 15–30x on a 0.1 μm Amicon filter and aliquoted to 0.5 ml volumes. Liposomes of reduced PC composition were produced by addition of increasing concentrations of lecithen or cholesterol (Sigma Chemical, St. Louis, MO) prior to sonication. The final PC composition was determined by inorganic phosphate precipitation. Contaminating multilamellar vesicles and homogeneously sized liposomes were isolated by molecular sieve chromatography as follows. A cross-linked Sepharose 4B column (Pharmacia Chemicals, Piscataway, N.J.) was prepared using endotoxin free reagents and equilibrated with buffer. The lipid mixture loaded on the column in 0.5 ml aliquots and slowly eluted with KCl-Tris buffer at 4° C. 1.0 ml fractions were collected and optical density of each fraction was determined at 320 nm. Using this procedure 95-98% unilamellar vesicles were routinely recovered in the second elution peak. Percentage of PC incorporated into the liposome was determined by inorganic phosphate precipitation. The liposomes in each fraction were characterized by plotting the absorbance at 20 nm as a function of total lipid concentration. A linear relationship between lipid concentration and absorbance which can be extrapolaed through the origin indicates that the liposomes are uniformly sized. Aliquots containing uniformly-sized liposomes were pooled and reconstituted in the desired buffer for dialysis or use in vitro.

Preparation of Purified C-Reactive Protein

CRP-rich acute phase serum was obtained from burn patients, and patients suffering from inflammatory diseases. Acute phase plasma was supplemented with $NaN_3$ to yield a final concentration of 0.1%. CRP concentration was determined by a radioimmunodiffusion assay (RID) using anti-CRP antibodies (Atlantic Antibodies, Lewiston, Me.) in 5-6% agar and aliquots >20 µg/ml CRP were pooled. $CaCl_2$ and $MgCl_2$ were added to yield a final concentration of 20mM. Aliquots of CRP rich sera were heated to 37° C. for 12 h with exposure to glass beads to promote clotting. Clots were removed by centrifugation at 280g for 10 min. Pooled aliquots of 1-2.25 L of CRP sera was passed through a 1.5×20 or 3×40 cm phosphorylcholine (PC) biogel column (Affinitech, San Diego, Ca.). Following passage of fluid, column was washed extensively with equilibration buffer (75 mM Tris-HCL, 0.15 M NaCl, 0.002 M $CaCl_2$ pH 7.3) for 48 h until $OD_{280}$ decreased below 0.05. CRP was eluted with elution buffer (75mM Tris, 7.5mM citrate, 0.15M NaCl, pH 7.3) Fractions were collected in 5 ml aliquots. Fractions with $OD_{280}$ above 0.35 were pooled and diluted 1:3 with pyrogen free water. DE52 resin (BioRad) was added at 50g/500ml of diluted plasma and slurry was packed into a large 3×60 cm column. CRP was purified by linear NaCl gradient of 0.05-6.0 M with 0.1M $PO_4$. Protein peaks were identified by microprotein assay against a bovine serum albumin standard (Biorad). The second protein peak (with a conductivity between 12-15 mmho) was collected and supplemented with $CaCl_2$ to a final concentration of 2 mM. Contaminating serum amyloid protein (SAP) was removed from CRP-rich pool by passage through a swollen Biogel A column. CRP rich eluant was dialyzed 4 times against 100 volumes of 15 mM NaCl 10 mM Tris buffered containing 2mM $CaCl_2$ at pH 7.3

Dialysate was filtered through 0.22 µM low protein binding filter (Amicon, Litton, N.J.). Aliquots were tested for bacterial lipopolysaccharide Limulus amoebocyte assay; LAL (Cape Cod Associates, Woods Hole, Mass.) and adjusted to ml aliquots containing 400 µg CRP. Aliquots were stored at 4° C.

Preparation of CRP bound liposomes

CRP opsonized liposomes were prepared by mixing a 40% v/v solution of PC liposomes with various concentrations of affinity-purified CRP for 1 h at 37° C. with end over end rocking (30 rpm). Following washes, liposomes were decanted and a 100 µl sample was stained with 1% Oil Red O (Sigma Chemical Co., St. Louis, Mo.), and counted on a bacterial sizing chamber (Haemonetics Inc., Brandfor, UK). CRP bound PC liposomes were adjusted to $1 \times 10^9$ liposome/ml and stored at 4° C.

Drug encapsulation in PC liposomes

Amphotercin B encapsulated CRP-PC liposomes were prepared immediately prior to experimentation. A stock solution of Amphotercin B was prepared at concentrations ranging from 10-100 µg/ml in endotoxin-free hyperosmolar phosphate buffered saline (PBS) (30 mM) and vigorously vortexed for 10 minutes at room temperature. Experimental liposomes, previously bound with different concentrations of C-reactive protein, were equilibrated for 5 min at room temperature in hyperosmolar phosphate buffered saline (PBS, 30 mM NaCl, 10 phosphate) containing different concentrations of Amphotercin B. Drug was encapsulated into liposomes by mild sonication at 4-6 cycles of 8 seconds (8-12% duty). Following drug incorporation, CRP-liposomes were washed in 21° C. 15 mM PBS (3×10 minutes) by gentle and over end rotation at 30 rpms. Following washes, liposomes were collected by Amicon filtration or aspiration and assayed for homogeneity by staining with Dragendorff's reagent or Orinoco red stain, and quantitated on a bacterial sizing chamber. Liposomes were adjusted to $1 \times 10^8$ and added to infected and control cells at a ratio of 100:1 (liposomes:-cell)

Isolation of PBMC

Heparinized blood (10 U/ml) was obtained by venupuncture from healthy human volunteers who had not been previously exposed to Leishmania or to trypanosomes, and who had not taken cyclooxygenase inhibitors within the last 7 days. Peripheral blood mononuclear cells (PBMCs) were isolated from heparinized blood by pyrogen free Ficoll-hypaque centrifugation (400 g, 45 mins, 21° C., d=1.079 g/ml). PBMCs were retrieved by gentle aspiration and washed three times in cold phosphate buffered saline (320 g, 4° C., 10 mins). Percentage monocytes and lymphocytes was determined by α-naphtyl acetate reduction stain, and contaminating population of polymorphonuclear cells was determined by Diff Quik stain (American Scientifid Products, McGraw Park, Ill.).

PBMC Cultures

For experiments requiring lymphocyte monocyte interactions, PBMCs were pelleted (320g, 10 mins, 4° C.) and resuspended in RPMI 1640 medium (Microbiological Associates) supplemented with 2mM L-glutamine (Irvine Scientific, Santa Ana, Calif.) 100 U penicillin/ml, 100 ug streptomycin/ml (Irvine Scientific, Santa Ana, Calif.) and 5% heat inactivated human AB or autologous serum. The mononuclear cell concentration was adjusted to $5 \times 10^6$/ml and 200 ul was dispensed into 4 ml polypropylene tubes. Cultures were incubated at 37° C. in a 5% $CO_2$/95% air, high humidity atmosphere prior to infection with leishmania or stimulation.

Long term PBMC cultures were incubated in 15 or 30 ml pyrogen-free teflon beakers (Savillex, Minnitonka, Mn.). In these experiments, following long term culture, cells were resuspended by gentle pipetting and washed twice in RPMI media prior to infection.

Monocyte/Macrophage Cultures

Select experiments requiring highly purified populations of monocytes or macrophages made use of countercurrent centrifugation elutriation. Briefly, 250 or 500 ml of blood was drawn into a heparinized syringe and PBMCs were isolated by ficoll-hypaque as previously described. PBMC were washed three times in PBS and adjusted to a concentration of $2.5 \times 10^7$ PBMCs/ml in elutriation media (PBS, 2% human albumin, 20 mM l-glutamine). PBMCs were infused at a flow rate of 6 mls/min into elutriation chamber (Beckman Model JE-6 elutriation system) spinning at 2020 rpms $+/-10$ rpm (Beckman J-6B centrifuge) set at 7° C. After infusion of PBMCs, the media flow rate was increased by 0.5 mls every 8 minutes until no more lymphocytes were observed exiting the elutriator. The remaining monocyte population was collected, washed three times in PBS and adjusted to $5 \times 10^6$/ml in RPMI 1640 media. Percentage monocytes was determined by $\alpha$-naphtyl esterase stain and viability was determined by trypan blue exclusion and latex bead phagocytosis. Purified monocytes were used directly in experiments or were placed in long term pyrogen-free teflon culture to obtain mature macrophage populations for experiments.

Macrophage cultures

Mature differentiated macrophages were obtained by long term culture of monocytes isolated by countercurrent centrifugation elutriation. Following isolation, pure monocytes were suspended at $1 \times 10^7$ cells/ml in RPMI 1640 media supplemented with 100 U penicillin/ml, 100 $\mu$g streptomycin/ml and 20 mM L-glutamine and 30% v/v autologous heat inactivated serum and 5% v/v human albumin. 10 mls of this suspension was placed in sterile, lipopolysaccharide-free teflon culture chambers and cultured for 14 or 21 days at 37° C. and 5% $CO_2$/95% air.

Liposome Uptake by Macrophage

FIG. 1 illustrates the results of an assay for uptake of coated an uncoated liposomes by macrophages. The liposomes were Lipisin II. They coated with various concentrations of CRP and exposed to macrophages. The macro phages were fixed and stained with Oil Red O to visualize ingested liposomes.

Parasites

Leishmania tropica major (World Health Organization strain designation MHOM/SN/74 Seidman) and Leishmania mexicana maria (NIH strain) were maintained by serial passage of amastigotes in footpads of BALB/c mice (Charles River Breeding Laboratories, Wilmington, Mass.) or axenic culture of promastigotes in cell culture.

Amastigotes

Amastigotes were harvested under sterile conditions from the footpad tissue of mice infected 6 weeks previously with $5 \times 10^5$ amastigotes into each hind footpad. Tissue was disrupted by compression with a syringe plunger through a sterile #60 stainless steel mesh. Cells were mechanically lysed by the forcible passage of the suspension through a 21, 23 and 25 gauge needle using a polypropylene syringe. The amastigote suspension was centrifuged at 160g for 10 min to sediment cell debris, and unlysed cells. Monodispersed parasites were retrieved in the supernatant and collected by centrifugation at 2100g for 10 min. Parasites were quantitated by a dilution technique using chicken erythrocytes of known concentration (DJW 16).

Promastigotes

Promastigote stages of L. mexicana maria and L. tropica major were maintained in axenic cultures maintained at 31° C. and 26° C., respectively. Primary cultures of promastigotes were established in sterile 75 cm polystyrene culture flasks (Costar, Cambridge, Mass.) by transfer of $1 \times 10^7$ amastigotes into 50 ml of RPMI 1640 media supplemented with 15 mM HEPES and 20% v/v fetal calf serum (Microbiological Associates). Promastigotes were passed every 9 to 11 days. Prior to use in experiments, promastigote culture supernatant was tested for bacterial contamination by 24h plating on tripticase soy agar or brain heat infusion agar (Microbiological Associates). Promastigotes were prepared for infection of human cells by first washing 3 times in PBS (2100 g, 10 min) and resuspended at $1 \times 10^7$ parasites/ml. Only sterile cultures in stationary phase were used in experiments.

Infection of cells

For experiments using amastigotes, purified monocytes/macrophages and PBMCs were infected at 2:1 and 2:5 multiplicity of infection (amastigotes:host cell). For experiments using promastigotes, multiplicity was 8:1 for monocyte/macrophages and 16:5 for PBMCs (promastigotes:host cells). Following addition of parasites, cultures were rocked gently for 1 hour at 37° C. and then transferred to 37° C., 5% $CO_2$ incubator for the duration of the experiment. At 24 hours of infection, representative samples of cells were collected to determine percent infection, and cells were returned to incubator. All cells were harvested at 72 h of infection and cytocentrifuged (Shandon-Southern, Swickley, Pa.) onto glass slides. Cells were stained with Wright's-Giemsa (Diff Quik, Baxter Health Care Products, Miami, Fl.). Slides were examined under oil immersion and percentage of macrophages infected and mean number of amastigotes per infected macrophage was determined. Antileishmanial and proleishmanial effects for different experiments and different experimental conditions were compared using the following formula: $100 \times (1 - $ mean number amastigotes per 100 treated macrophages/ mean number amastigotes per 100 control macrophages).

Figure 2:
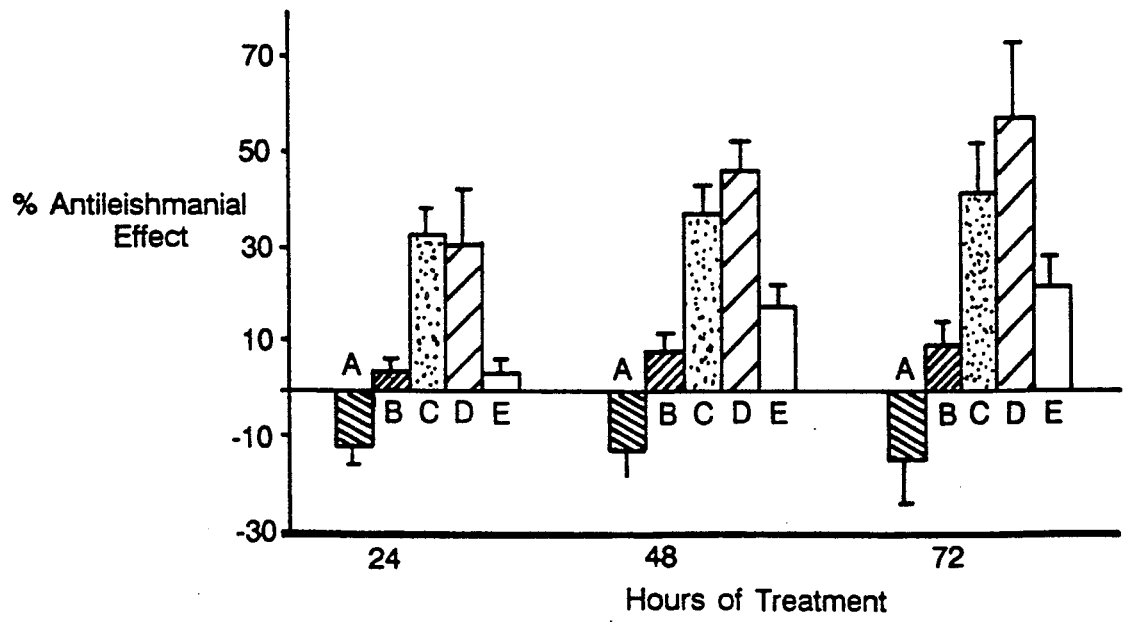
FIG. 2 depicts a graph which illustrates the anti-leshmanial effect of various treatments after 24, 48, and 72 hours of treatment. Leishmanial infected monocytes were treated with liposomes only (A), C-reactive protein only (B), liposomes and C-reactive protein (C), emphotericin encapsulated liposomes coated with C-reactive protein (D), or amphotericin encapsulated liposomes (E).

Differences in mean number of intracellular parasites per 100 macrophages under various experimental conditions was analyzed statistically using the STATVIEW TM 512 one-way analysis of variance program. The results are presented in FIG. 2.

Use

The coated liposomes can be infused intravenously. Preferably the concentration of liposome is less than 20% in saline. Drugs will be used ad dosages which are much lower than used routinely.

We claim:

1. A method for treating an infection caused by an intracellular bacteria in a patient said method comprising administering to said patient liposomes coated with C-reactive protein, wherein said liposomes comprise phosphatidylcholine or phosphorylcholine.

2. The method of claim 1 wherein said intracellular parasite is a mycobacteria.

3. The method of claim 1 wherein said intracellular parasite is mycobacterium avium intracellulare.

4. The method of claim 1 wherein said intracellular parasite is mycobacterium tuberculosis.

* * * * *

UNITED STATES PATENT AND TRADEMARK OFFICE
CERTIFICATE OF CORRECTION

PATENT NO.   : 5,270,052					Page 1 of 2

DATED        : Dec/14/93

INVENTOR(S)  : Jeffrey A. Gelfand, Michael V. Callahan, and
               Yoshinori Yamada It is certified that error appears in the above-identified patent and that said Letters Patent is hereby corrected as shown below:

Col. 1, lines 52 and 53, replace "a 5 mycobacteria" with --a mycobacteria--;

Col. 3, lines 52 and 53, replace "inculation" with --incubation--;

Column 4, line 66, replace "lecithen" with --lecithin--;

Column 5, line 15, replace "20 nm" with --320 nm--;

Column 5, line 67, replace "ml" with --1 ml--;

Column 6, line 51, replace "naphtyl" with --naphthal--;

Column 6, line 53, replace "Scientifid" with --Scientific--;

Column 7, line 25, replace "naphtyl" with --naphthal--;

UNITED STATES PATENT AND TRADEMARK OFFICE
CERTIFICATE OF CORRECTION

PATENT NO. : 5,270,052

DATED : Dec. 14, 1993

INVENTOR(S) : Jeffrey A. Gelfand, MIchael V. Callahan, and Yoshinori Yamada

It is certified that error appears in the above-indentified patent and that said Letters Patent is hereby corrected as shown below:

Column 7, line 50, replace "macro phages" with --macrophages--.

Signed and Sealed this

Twenty-fourth Day of May, 1994

*Attest:*

BRUCE LEHMAN

*Attesting Officer*   *Commissioner of Patents and Trademarks*